United States Patent [19]

Barclay et al.

[11] 4,380,681
[45] Apr. 19, 1983

[54] HYDROCARBONYLATION OF METHANOL TO ETHANOL IN THE PRESENCE OF ADDED COMPOUNDS

[75] Inventors: John L. Barclay, Tadworth; Brian R. Gane, Weybridge, both of England

[73] Assignee: The British Petroleum Company Limited, London, England

[21] Appl. No.: 210,547

[22] Filed: Nov. 26, 1980

Related U.S. Application Data

[63] Continuation of Ser. No. 52,006, Jun. 25, 1979, abandoned, which is a continuation of Ser. No. 908,060, May 22, 1978, abandoned.

[30] Foreign Application Priority Data

May 27, 1977 [GB] United Kingdom ............... 22490/77

[51] Int. Cl.$^3$ ............................................. C07C 29/00
[52] U.S. Cl. .................................................. 568/902
[58] Field of Search .......................................... 568/902

[56] References Cited

U.S. PATENT DOCUMENTS

| | | | |
|---|---|---|---|
| 2,623,906 | 12/1952 | Gresham | 568/902 |
| 3,248,432 | 4/1966 | Riley et al. | 568/902 |
| 3,285,948 | 11/1966 | Butter | 568/902 |
| 4,111,837 | 9/1978 | Taylor | 568/902 |
| 4,150,246 | 4/1979 | Taylor | 568/902 |

FOREIGN PATENT DOCUMENTS 951506 3/1964 United Kingdom ................ 568/902

OTHER PUBLICATIONS

Wender et al., "Science", vol. 113 (1951), pp. 206–207.

*Primary Examiner*—Joseph E. Evans
*Attorney, Agent, or Firm*—Brooks, Haidt, Haffner & Delahunty

[57] ABSTRACT

Ethanol is produced by reacting methanol with carbon dioxide and hydrogen at a temperature in the range 150° to 250° C., a pressure in the range 100 to 300 bars and a residence time in the range 10 minutes to 8 hours in the presence of:

(i) a cobalt-containing catalyst optionally promoted with iodine, bromine or an organo-phosphorus compound and optionally in the presence of a stabilizer and, (ii) an additive which may be a monocarboxylic acid and/or a derivative thereof and, optionally, a non-polar solvent such as an alkane, benzene or an alkyl-substituted benzene.

The preferred additives are acetic acid and methyl acetate. The presence of the additive increases the total realizable yield and selectivity to ethanol.

23 Claims, 1 Drawing Figure

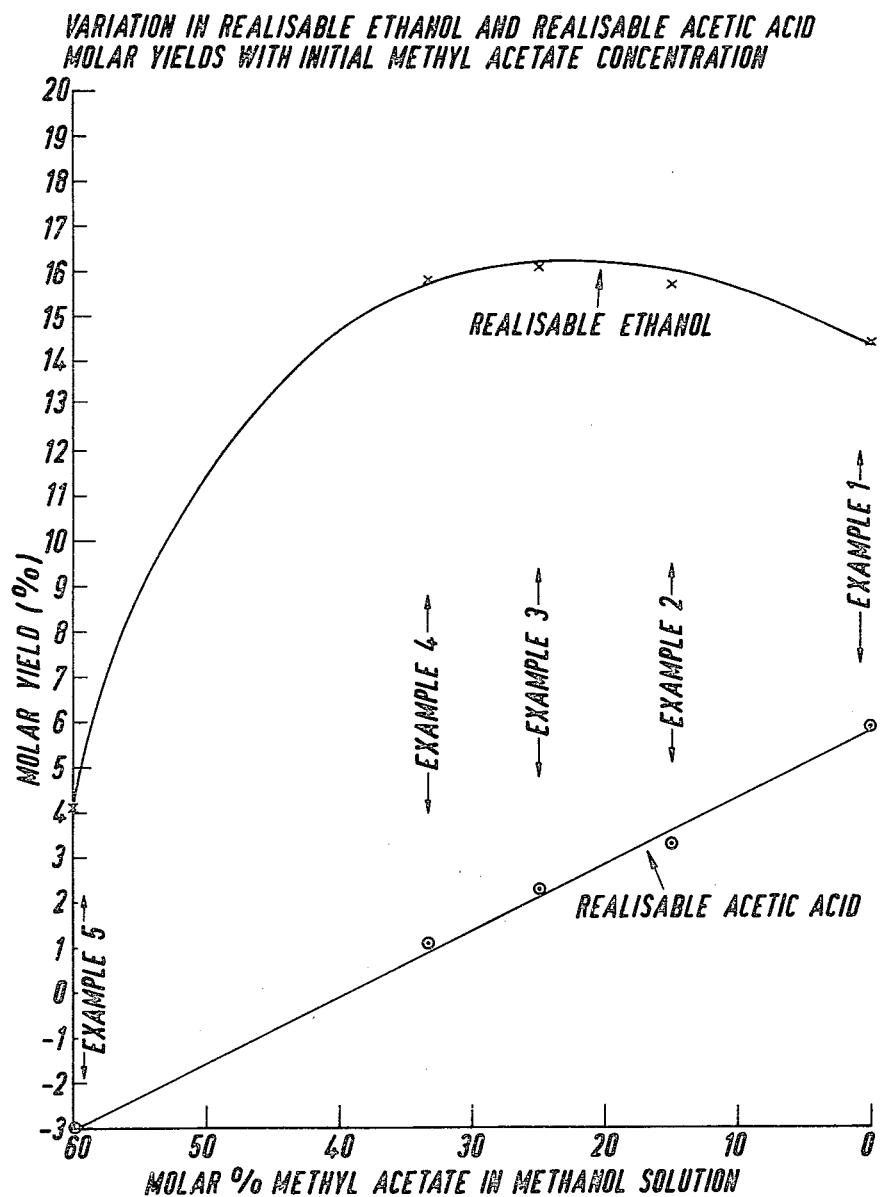

HYDROCARBONYLATION OF METHANOL TO ETHANOL IN THE PRESENCE OF ADDED COMPOUNDS

This is a continuation of application Ser. No. 052,006, filed June 25, 1979, now abandoned, which in turn is a continuation of Ser. No. 908,060, filed May 22, 1978, now abandoned.

The present invention relates to the production of ethanol from methanol and synthesis gas (mixtures of carbon monoxide and hydrogen) in the presence of a cobalt-containing catalyst.

Ethanol is a valuable industrial product which is generally manufactured either by fermentation of natural products, eg molasses or by hydration of ethylene in the presence of an acid catalyst, such as phosphoric acid. The rapidly dwindling reserves of crude oil from which ethylene is derived and the associated need to utilise fully the remaining natural resources such as coal and the vast amounts of gases, eg the methane potentially available from the exploitation of North Sea oilfields, has stimulated researchers to investigate other routes to ethanol utilising these materials as feedstocks. Both coal and methane gas can be converted into synthesis gas ($CO+H_2$), which in turn can be reacted to form methanol, which can be further reacted with carbon monoxide and hydrogen under appropriate conditions to form ethanol.

It has long been known that methanol can be hydrocarbonylated with hydrogen and carbon monoxide to ethanol in the presence of a water soluble cobalt catalyst at high temperatures and pressures. The course of this reaction can be represented by the following equation:

$$CH_3OH + CO + 2H_2 \rightarrow C_2H_5OH + H_2O$$

Thus in a paper published in Science 113, 206 (1951) Wender, Friedel and Orchin reported that methanol was reacted with synthesis gas ($1H_2:1CO$) in the presence of dicobalt octacarbonyl as catalyst to produce methyl formate (2%), methyl acetate (9.0%), ethyl alcohol (38.8%), ethyl acetate (6.3%), propyl alcohol (4.7%), butyl alcohol (0.9%), methane (8.5%), propyl acetate (0.1%) and a small amount of unidentified product, the total conversion of methanol being 76.4%.

The problem with this and the majority of prior art processes is that they produce large amounts of by-products such as esters, and acids in addition to ethanol.

We have now found that the total realisable yield and selectivity to ethanol, as hereinafter defined, can be increased by the addition of certain acids and acid derivatives. These additives suppress or inhibit the formation of undesirable byproducts, such as acids (eg acetic acid) and derivatives thereof (eg methyl acetate).

By total realisable yield of ethanol within the context of the present specification is meant the yield of free ethanol plus the yield of ethanol realisable by the hydrolysis of ethanol-yielding esters (eg ethyl acetate). In the same way, by the total methanol is meant the free methanol plus the methanol realisable by the hydrolysis of methanol-yielding esters (eg methyl acetate).

Thus, the % Molar Yield of Realisable Ethanol $$= \frac{\text{Moles of methanol converted into realisable ethanol}}{\text{Total moles of methanol fed}} \times 100$$

and the % Molar Selectivity to Realisable Ethanol $$= \frac{\text{Moles of methanol converted into realisable ethanol}}{\text{Total moles of methanol converted}} \times 100$$

By the yield of realisable acetic acid is meant the yield of free acetic acid plus the yield of acetic acid realisable by the hydrolysis of acetic acid-yielding esters (eg methyl acetate). In calculating the yield it is assumed that all the acetic acid is derived from methanol and synthesis gas and no account is taken of acetic acid derived from cobalt acetate when this is added as catalyst.

Thus, the % Molar Yield of Realisable Acetic Acid $$= \frac{\text{Moles of methanol converted into realisable acetic acid}}{\text{Total moles of methanol fed}} \times 100$$

Methanol Conversion $$= \frac{\text{Total moles of methanol converted}}{\text{Total moles of methanol fed}} \times 100$$

Thus the present invention provides a process for the production of ethanol which process comprises contacting a mixture of methanol and synthesis gas at elevated temperature and pressure with a cobalt-containing catalyst in the presence of an additive comprising a monocarboxylic acid and/or a derivative thereof, which additive has the formula:

$$R-C\underset{X}{\overset{O}{\nearrow\!\!\!\!\!\diagdown}} \qquad (I)$$

wherein the substituent R is a hydrocarbyl group or an oxygen-containing hydrocarbyl group and the substituent X is the group —$OR^1$ in which $R^1$ is independently a hydrogen atom, a hydrocarbyl group or an oxygen-containing hydrocarbyl group or X is the group —O—CO—$R^2$ in which $R^2$ is independently a hydrocarbyl group or an oxygen-containing hydrocarbyl group.

Methanol is a readily available industrial product. It is generally manufactured on an industrial scale from synthesis gas. Whilst it is preferred that the methanol be substantially pure, the presence of small amounts of certain impurities can be tolerated. The methanol may however contain up to 50% by weight of water.

Mixtures of the gases hydrogen and carbon monoxide are abundantly available in the form of synthesis gas. Methods for preparing synthesis gas are well-known in the art and usually involve the partial oxidation of a carbonaceous substance, eg coal. Alternatively synthesis gas may be prepared, for example, by thermal steam reforming of methane. For the purpose of the present invention the molar ratio of carbon monoxide to hydrogen may suitably be in the range 2:1 to 1:3, preferably 1:1 to 1:2. Methods for adjusting the molar ratio of carbon monoxide to hydrogen are well-known to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

The cobalt-containing catalyst may be added directly, eg in the form of dicobalt octacarbonyl, which may be prepared by heating an anhydrous cobalt compound in a non-aqueous solvent at a temperature greater than 100° C. and in a superatmosphere of carbon monoxide and hydrogen. Alternatively the cobalt-containing catalyst may be formed 'in situ' under the prevailing reaction conditions by simply adding a soluble cobalt compound to the initial reaction mixture. It is believed that the active catalyst species is dicobalt octacarbonyl but we do not wish to be bound in any way by this belief. Whilst any soluble cobalt compound which gives rise to dicobalt octacarbonyl under the reaction conditions may be employed it is preferred to add cobaltous acetate either in the hydrated or anhydrous form. The amount of catalyst present may suitably be sufficient to provide a cobalt to methanol molar ratio in the range 1:10 to 1:1000, preferably 1:40 to 1:800. In addition to the catalyst a promoter may optionally be incorporated in the reaction mixture. Suitable promoters include iodine, bromine and certain organo-phosphorus compounds. The iodine or bromine may be added in either the ionic form, ie as an iodide or bromide, or in the molecular form, ie as molecular iodine or bromine. The molar ratio of cobalt to iodine or bromine may suitably be in the range 1:3 to 10:1, preferably 1:1 to 5:1. The molar ratio of cobalt to organophosphorus compound may suitably be in the range 1:10 to 6:1. At the higher reaction temperatures it may also be advantageous to include in the reaction mixture small amounts of a catalyst stabiliser. Stabilisers which may be used, for example, include those disclosed in U.S. Pat. No. 3,931,332 to Chevron Research Company.

Whilst it is appreciated that monocarboxylic acids and derivatives thereof may be formed as by-products during the course of the hydrocarbonylation reaction the invention resides in the addition of such compounds to the reaction mixture. Accordingly the term 'additive' is used herein to mean a compound which is added to the reaction mixture as distinct from one which is formed during the reaction. It is found that by so-doing the amount of unwanted side reaction is reduced, with the attendant consequence that the total selectivity to ethanol is increased. Preferably the additive is one which exists mainly in the form of a liquid under the prevailing reaction conditions. With reference to the formula (I) R, $R^1$ and $R^2$ may independently be hydrocarbyl groups or oxygen-containing hydrocarbyl groups. As used in this specification the term 'hydrocarbyl' is used in its generally accepted sense as meaning a radical formed from a hydrocarbon by removal of a hydrogen atom. The hydrocarbyl group is preferably free from aliphatic carbon-carbon unsaturation. Suitably the hydrocarbyl group may be a saturated aliphatic group, a saturated cycloaliphatic group or an aromatic group. Preferably the hydrocarbyl group is a saturated aliphatic group. Preferably the saturated aliphatic group is an alkyl group containing from 1 to 20, preferably from 1 to 6 carbon atoms. The substituent X in the formula (I) may be either an alkoxy group $—OR^1$, in which case the additive is an ester, or a hydroxyl group —OH, in which case the additive is a monocarboxylic acid, or a carboxyl group $—O—CO—R^2$, in which case the additive is an acid anhydride. Preferably the substituent X is the group $—OR^1$ in which $R^1$ is either a hydrogen atom or an alkyl group containing from 1 to 20, preferably from 1 to 6 carbon atoms. Suitable additives having the formula (I) include acetic acid, acetic anhydride, methyl acetate, propionic acid, phenylacetic acid, decanoic acid, benzoic acid and butyl acetate. Preferred additives having the formula (I) are acetic acid and methyl acetate. It will of course be appreciated that when the compound of formula (I) is the free acid or anhydride it will largely be present in the reaction mixture as an ester by reaction with methanol, ethanol or other alcohol.

In addition to the monocarboxylic acid and/or derivative thereof essential to the invention there may also be added non-polar solvents such as alkanes, benzene and alkyl-substituted benzenes, as disclosed in U.S. Pat. application Ser. No. 585,276.

The mixture of synthesis gas and methanol is suitably contacted with the catalyst at an elevated temperature in the range of from 150° to 250° C., preferably from 175° to 230° C. and at an elevated pressure greater than 100, preferably 140 to 300 bars. At temperatures in excess of 200° C. and/or at low pressures it may be necessary to use a catalyst stabiliser as hereinbefore described.

The monocarboxylic acid and/or derivative thereof of formula (I) may suitably be added in an amount such that the molar ratio of additive to free methanol contacted with the catalyst is in the range from 0.1:1 to 0.7:1 but may be as high as 1.5:1. The molar ratio of methanol to synthesis gas fed may be in the range of from 10:1 to 1:20, preferably from 2:1 to 1:5.

The process may be carried out batchwise or continuously, continuous operation being preferred. The process may be carried out continuously for example by:

(A) continuously feeding methanol and synthesis gas to a reactor containing the catalyst and the additive, (B) removing from the reactor a liquid product containing ethanol, additive, by-products, unchanged methanol, catalyst and unreacted synthesis gas, (C) separating the synthesis gas which may be recycled to the reactor and removing light ends, (D) separating the product containing ethanol, additive and by-products from the catalyst and thereafter recovering ethanol therefrom, and (E) recycling to the reactor the catalyst, methanol and the additive.

Other reaction by-products particularly those which can act as precursors for the formation of ethanol such as acetaldehyde and 1,1-dimethoxyethane may also be recycled to the reactor with advantage. It may be necessary to feed from time to time further catalyst and to periodically adjust the amount of monocarboxylic acid and/or derivatives thereof in the system.

The residence time may suitably be up to 8 hours, but is preferably in the range of from 10 to 180 minutes. Within the context of the specification the residence time for batchwise operation is that time during which the reactor is at the specified reaction temperature. When the process is operated continuously the residence time is calculated as follows:

$$= \frac{\text{Volume of the reactor occupied by the liquid phase at STP (liters)}}{\text{Total flow of liquid into the reactor (liters/hour at STP)}}$$

The following Examples will now serve to illustrate the process of the invention.

EXAMPLE 1

A stainless steel, magnetically-stirred autoclave equipped for pressurised reactions was charged with methanol (8 moles) containing cobalt acetate tetrahydrate $Co(OAc)_2 4H_2O$ ($100 \times 10^{-3}$ moles). The system was purged with nitrogen, then pressurised to 200 bars with a mixture of carbon monoxide and hydrogen (1:1 molar). The reactor temperature was raised to 185° C. and maintained at this temperature for 2 hours. When heating was started the pressure in the reactor rose above 200 bars and then began to decrease as the reaction commenced. During the course of the reaction, whenever the pressure in the autoclave fell to 140 bars a fresh charge of carbon monoxide and hydrogen (1:1 molar mixture) was added thereby increasing the reactor pressure to 200 bars. After two hours at 185° C. the autoclave was allowed to cool and the reaction product was found to contain realisable ethanol (1.15 moles), realisable acetic acid (0.47 moles) together with other by-products such as dimethyl ether, methyl ethyl ether, acetaldehyde, 1,1-dimethoxy ethane, n-propanol and n-butanol. The results from this standard experiment (Example 1) are summarised in Table 1. This Example is not an example according to the invention and is included for the purpose of comparison only.

THE ADDITION OF METHYL ACETATE

EXAMPLE 2

The procedure of Example 1 was repeated except that methyl acetate was added to the methanol/cobalt acetate tetrahydrate solution charge.

The amounts of reactants, the reaction conditions and results are given in Table 1.

EXAMPLE 3

The procedure of Example 2 was followed with the amounts of reactants, the reaction conditions and the results shown in Table 1.

EXAMPLE 4

The procedure of Example 2 was followed with the amounts of reactants, the reaction conditions and the results shown in Table 1.

EXAMPLE 5

The procedure of Example 2 was followed with the amounts of reactants, the reaction conditions and the results shown in Table 1.

THE ADDITION OF IODINE

EXAMPLE 6

The procedure of Example 1 was followed except that iodine was added to the methanol/cobalt acetate tetrahydrate solution charge.

The amounts of reactants, reaction conditions and results are given in Table 1. This Example is not an example according to the present invention and is included for the purpose of comparison only.

EXAMPLE 7

The procedure of Example 1 was followed except that iodine and methyl acetate were added to the methanol/cobalt tetrahydrate solution charge.

The amounts of reactants, reaction conditions and results are given in Table 1.

EXAMPLE 8

The procedure of Example 7 was followed with the amounts of reactants, the reaction conditions and the results shown in Table 1.

TABLE 1

| EXAMPLE | Methanol added (moles) | Catalyst Precursor added in the form of $Co(OAc)_2 4H_2O$ (Moles $\times 10^{-3}$) | Additive and amount added (moles) | Residence Time (Hours) | Reaction Temperature (°C.) | Methanol Conversion (%) | Molar yield Realisable Ethanol (%) | Molar yield Realisable Acetic Acid (%) | Molar Selectivity to realisable Ethanol (%) |
|---|---|---|---|---|---|---|---|---|---|
| 1 not according to the invention | 8.0 | 100 | None | 2 | 185 | 36.8 | 14.4 | 5.9 | 39.1 |
| 2 | 6.8 | 100 | Methylacetate 1.2 | 2 | 185 | 33.4 | 15.7 | 3.3 | 47.0 |
| 3 | 6.0 | 100 | Methylacetate 2.0 | 2 | 185 | 30.6 | 16.1 | 2.3 | 52.6 |
| 4 | 4.0 | 75 | Methylacetate 2.0 | 2 | 185 | 23.8 | 15.8 | 1.1 | 66.4 |
| 5 | 1.6 | 50 | Methylacetate 2.4 | 2 | 185 | 7.8 | 4.1 | −3.0 | 32.6 |
| 6 not according to the invention | 2.0 | 25 | Iodine 0.025 | 2 | 185 | 61.5 | 12.9 | 13.0 | 21.0 |
| 7 | 4.0 | 75 | Methylaceate 2.0 Iodine 0.075 | 2 | 185 | 50.5 | 20.2 | 4.3 | 40.0 |
| 8 | 1.6 | 50 | Methylacetate 2.4 Iodine 0.050 | 2 | 185 | 36.5 | 21.3 | 3.4 | 58.4 |

Examples 2 to 5 show the effect of adding varying amounts of methyl acetate on the homologation of methanol to ethanol. In Examples 2 to 4 the molar yield of realisable ethanol increased whilst the molar yield of realisable acetic acid decreased, when compared with Example 1 in which no methyl acetate was added. In Example 5 the molar yield of realisable acetic acid is negative, indicating that some of the methyl acetate reacted to give a product which does not yield acetic acid. In all the Examples 2 to 5 in which methyl acetate was added the molar selectivity to realisable ethanol increased when compared with Example 1 in which there was no addition of methyl acetate.

Comparing Example 1 with Example 6, neither of which are examples of the present invention, it can be seen that the addition of iodine increases the methanol conversion but decreases the molar selectivity to realisable ethanol. Comparing Example 6 in which only iodine was added with Examples 7 and 8 in which both iodine and methyl acetate were added it can be seen that the addition of methyl acetate again improves the molar yield of realisable ethanol, decreases the molar yield of realisable acetic acid and increases the molar selectivity to realisable ethanol.

The amounts of reactants, the reaction conditions and the results obtained are given in Table 2.

EXAMPLE 13

The procedure of Example 1 was repeated except that phenylacetic acid was added to the methanol/cobalt acetate tetrahydrate solution charge.

The amounts of reactants, the reaction conditions and the results obtained are given in Table 2.

EXAMPLE 14

The procedure of Example 1 was repeated except that decanoic acid was added to the methanol/cobalt acetate tetrahydrate solution charge.

The amounts of reactants, the reaction conditions and the results obtained are given in Table 2.

TABLE 2

THE ADDITION OF ACIDS AND ACID DERIVATIVES OTHER THAN METHYLACETATE

| EXAMPLE | Methanol added (moles) | Catalyst Precursor added in the form of $Co(OAc)_2 4H_2O$ (Moles $\times 10^{-3}$) | Additive and amount added (moles) | Residence Time (Hours) | Reaction Temperature (°C.) | Methanol Conversion (%) | Molar yield Realisable Ethanol (%) | Molar yield Realisable Acetic Acid (%) | Molar Selectivity to realisable Ethanol (%) |
|---|---|---|---|---|---|---|---|---|---|
| 9 | 5.0 | 63 | Acetic Acid 1.67 | 2 | 185 | 21.6 | 14.3 | −0.2 | 66.2 |
| 10 | 3.0 | 38 | Acetic Acid 3.0 | 2 | 185 | 13.7 | 7.3 | −10.0 | 53.3 |
| 11 | 3.0 | 56 | Butyl Acetate 1.5 | 2 | 185 | 30.0 | 15.4 | 3.0 | 51.3 |
| 12 | 4.0 | 38 | Benzoic Acid 1.5 | 2 | 185 | 24.5 | 11.9 | 4.5 | 48.6 |
| 1 not according to the invention | 8.0 | 100 | None | 2 | 185 | 36.8 | 14.4 | 5.9 | 39.1 |
| 13 | 5.0 | 63 | Phenylacetic Acid 0.75 | 2 | 185 | 30.5 | 13.0 | 4.0 | 42.6 |
| 14 | 4.5 | 56 | Decanoic Acid 0.675 | 2 | 185 | 25.6 | 16.7 | 4.6 | 65.2 |

THE ADDITION OF ACIDS AND ACID DERIVATIVES OTHER THAN METHYLACETATE

EXAMPLE 9

The procedure of Example 1 was repeated except that acetic acid was added to the methanol/cobalt acetate tetrahydrate solution charge.

The amounts of reactants, the reaction conditions and the results are given in Table 2.

EXAMPLE 10

The procedure of Example 9 was followed with the amounts of reactants, the reaction conditions and the results shown in Table 2.

EXAMPLE 11

The procedure of Example 1 was repeated except that butyl acetate was added to the methanol/cobalt acetate tetrahydrate solution charge.

The amounts of reactants, the reaction conditions and the results obtained are given in Table 2.

EXAMPLE 12

The procedure of Example 1 was repeated except that benzoic acid was added to the methanol/cobalt acetate tetrahydrate solution charge.

By reference to Table 2 it can be seen that adding acetic acid (Examples 9 and 10), butyl acetate (Example 11), benzoic acid (Example 12), phenylacetic acid (Example 13) and decanoic acid (Example 14) increases the molar selectivity to realisable ethanol over that obtained in Example 1 in which there was no such addition.

THE ADDITION OF ACIDS AND ACID DERIVATIVES WITH AN 8-HOUR RESIDENCE TIME

EXAMPLE 15

Example 1 was repeated except that the residence time was increased from 2 to 8 hours.

The amounts of reactants, the reaction conditions and results obtained are given in Table 3. Example 15 is not an example according to the invention and is included for the purpose of comparison only.

EXAMPLE 16

The procedure of Example 15 was repeated except that acetic acid was added to the methanol/cobalt acetate tetrahydrate solution charge.

The amounts of reactants, the reaction conditions and the results obtained are given in Table 3.

EXAMPLE 17

The procedure of Example 15 was repeated except that methyl acetate was added to the methanol/cobalt acetate tetrahydrate solution charge.

The amounts of reactants, the reaction conditions and the results obtained are given in Table 3.

EXAMPLE 18

The procedure of Example 15 was repeated except that propionic acid was added to the methanol/cobalt acetate tetrahydrate solution charge.

The amounts of reactants, the reaction conditions and the results obtained are given in Table 3.

TABLE 3

| | | | | | | | | | |
|---|---|---|---|---|---|---|---|---|---|
| THE ADDITION OF ACIDS AND ACID DERIVATIVES WITH AN 8-HOUR RESIDENCE TIME | | | | | | | | | |
| EXAMPLE | Methanol added (moles) | Catalyst Precursor added in the form of $Co(OAc)_2 4H_2O$ (Moles $\times 10^{-3}$) | Additive and amount added (moles) | Residence Time (Hours) | Reaction Temperature (°C.) | Methanol Conversion (%) | Molar yield Realisable Ethanol (%) | Molar yield Realisable Acetic Acid (%) | Molar Selectivity to realisable Ethanol (%) |
| 15 not according to the invention | 8.0 | 94 | None | 8 | 185 | 46.6 | 19.9 | 10.6 | 42.7 |
| 16 | 1.0 | 23 | Acetic Acid 0.5 | 8 | 185 | 43.7 | 28.7 | −3.4 | 65.7 |
| 17 | 1.0 | 23 | Methylacetate 0.5 | 8 | 185 | 54.0 | 29.1 | 0.7 | 53.9 |
| 18 | 4.0 | 50 | Propionic Acid 2.0 | 8 | 185 | 36.0 | 29.6 | 5.9 | 82.2 |

By reference to Table 3 it can be seen that at the higher residence time the addition of acetic acid (Example 16), methyl acetate (Example 17) and propionic acid (Example 18) all increase the molar yield of realisable ethanol, decrease the molar yield of realisable acetic acid and increase the molar selectivity to realisable ethanol when compared with Example 15, which is not an example according to the invention.

In order to demonstrate more clearly the improvement in the total realisable yield of ethanol achieved by operation of the process according to the invention the results of Examples 1 to 5, shown in Table 1, are represented graphically in the FIGURE as a plot of total realisable yields of ethanol and acetic acid versus the molar % methyl acetate in methanol solution.

We claim:

1. A process for the production of ethanol which process comprises contacting a mixture of methanol and synthesis gas at elevated temperature and pressure with a cobalt-containing catalyst in the presence of an additive which is deliberately added to the reaction system, said additive being selected from the group consisting of monocarboxylic acids and derivatives thereof having the formula

wherein the substituent R is selected from hydrocarbyl groups and oxygen-containing hydrocarbyl groups and the substituent X is selected from the groups $-OR^1$ and $-O-CO-R^2$ in which $R^1$ is selected from the group consisting of a hydrogen atom, a hydrocarbyl group and an oxygen-containing hydrocarbyl group and $R^2$ is selected from the group consisting of a hydrocarbyl group and an oxygen-containing hydrocarbyl group, said additive of formula I being added in an amount such that the molar ratio of additive to free methanol contacted with the catalyst is in the range of from 0.1:1 to 1.5:1, provided that when R and $R^1$ are both methyl then the molar ratio of additive to free methanol contacted with the catalyst is in the range of from about 0.1:1 to 0.7:1.

2. A process as claimed in claim 1 wherein said synthesis gas consists of carbon monoxide and hydrogen in a molar ratio in the range 2:1 to 1:3.

3. A process according to claim 1 wherein said cobalt-containing catalyst is added directly in the form of dicobalt octacarbonyl.

4. A process according to claim 1 wherein said cobalt-containing catalyst is formed 'in situ' under the prevailing reaction conditions by adding a soluble cobalt compound to said initial reaction mixture.

5. A process according to claim 1 wherein the amount of said catalyst present is sufficient to provide a cobalt to methanol molar ratio in the range 1:10 to 1:1000.

6. A process according to claim 1 wherein, in addition to said catalyst, a promoter selected from iodine, bromine and organophosphorus compounds is incorporated in said reaction mixture.

7. A process according to claim 6 wherein said promoter is iodine and the molar ratio of cobalt to iodine is in the range 1:3 to 10:1.

8. A process according to claim 1 wherein said additive exists mainly in the form of a liquid under said prevailing reaction conditions.

9. A process according to claim 1 wherein said hydrocarbyl groups in said additive of formula (I) are individually selected from saturated aliphatic groups, saturated cycloaliphatic groups and aromatic groups.

10. A process according to claim 1 wherein said hydrocarbyl groups in said additive of formula (I) are individually selected from alkyl groups containing from 1 to 20 carbon atoms.

11. A process according to claim 1 wherein said substituent X in said additive of formula (I) is the group $-OR^1$ in which $R^1$ is selected from alkyl groups containing from 1 to 20 carbon atoms.

12. A process according to claim 1 wherein said substituent X in said additive of formula (I) is the group $-OR^1$ in which $R^1$ is a hydrogen atom.

13. A process according to claim 1 wherein said additive is acetic acid.

14. A process according to claim 1 wherein said additive is methyl acetate.

15. A process according to claim 1 wherein, in addition to said additive, there is added a non-polar solvent selected from alkanes, benzene and alkyl-substituted benzenes.

16. A process according to claim 1 wherein said elevated temperature is in the range of from 150° to 250° C.

17. A process according to claim 1 wherein said elevated pressure is in the range of from 100 to 300 bars.

18. A process according to claim 1 wherein the molar ratio of said methanol to said synthesis gas in said feed mixture is in the range of from 10:1 to 1:20.

19. A process according to claim 1 wherein ethanol is produced by the steps comprising:
(A) continuously feeding said methanol and said synthesis gas to a reactor containing said catalyst and said additive, said reactor being maintained at said elevated temperature and pressure,
(B) removing from said reactor a liquid product containing ethanol, by-products, unchanged methanol, unreacted synthesis gas, said additive and said catalyst,
(C) separating said unreacted synthesis gas and a light fraction of said by-products from said product of step (B), leaving a residual product containing ethanol, said catalyst, said additive, said unchanged methanol and the remainder of said by-products,
(D) separating said residual product from step (C) into ethanol, said catalyst, said additive, said unchanged methanol and the remainder of said by-products,
(E) recycling to said reactor said catalyst, said additive and said unchanged methanol separated in step (D).

20. A process according to claim 1 wherein the residence time is in the range of from 10 minutes to 8 hours.

21. A process as defined in claim 1 wherein said additive is methyl acetate, acetic acid, propionic acid, phenylacetic acid, decanoic acid, benzoic acid, or butyl acetate.

22. A process as defined in claim 1 wherein said additive is propionic acid, phenyl acetic acid, decanoic acid, benzoic acid, or butyl acetate.

23. A process as defined in claim 1 wherein said additive is phenylacetic acid, decanoic acid, or benzoic acid.

* * * * *